United States Patent [19]
Kikumoto et al.

[11] 4,284,637
[45] Aug. 18, 1981

[54] PHARMACEUTICALLY ACTIVE 2-(4-AMINOBUTOXY)STILBENES

[75] Inventors: Ryoji Kikumoto, Machida; Akihiro Tobe, Kawasaki; Harukazu Fukami, Yokohama; Kunihiro Ninomiya, Yokohama; Mitsuo Egawa, Yokohama, all of Japan

[73] Assignee: Mitsubishi Chemical Ind., Limited, Tokyo, Japan

[21] Appl. No.: 80,215

[22] Filed: Oct. 1, 1979

Related U.S. Application Data

[62] Division of Ser. No. 11,998, Feb. 14, 1979, Pat. No. 4,217,366.

[51] Int. Cl.$^3$ .................. A61K 31/40; A61K 31/445; A61K 31/495; C07D 221/00

[52] U.S. Cl. .................. 424/267; 424/250; 424/274; 542/459

[58] Field of Search .................. 424/267; 542/459

[56] References Cited

U.S. PATENT DOCUMENTS

| 2,485,662 | 10/1949 | Rohrmann | 542/459 |
| 2,971,001 | 2/1961 | Rohrmann | 542/459 |
| 3,077,470 | 2/1963 | Burckholler | 542/459 |

Primary Examiner—Stanley J. Friedman
Attorney, Agent, or Firm—Oblon, Fisher, Spivak, McClelland & Maier

[57] ABSTRACT 2-(4-aminobutoxy)stilbenes are prepared and found useful as pharmaceutical agents, particularly as anticonvulsants and skeletal muscle relaxants.

7 Claims, No Drawings

PHARMACEUTICALLY ACTIVE 2-(4-AMINOBUTOXY)STILBENES

This is a division of application Ser. No. 011,998, filed Feb. 14, 1979, now U.S. Pat. No. 4,217,366.

BACKGROUND OF THE INVENTION

1. Field of the Invention

This invention relates to 2-(4-aminobutoxy)stilbenes and their acid addition salts which are pharmacologically active as anticonvulsants and skeletal muscle relaxants.

2. Description of the Prior Art

British Pat. No. 1,307,436 discloses 2-(2-aminoethoxy)stilbenes and 2-(3-aminopropoxy)stilbenes, which possess analgesic activity, while they do not possess anticonvulsant activity which is a characteristic feature of the compounds of this invention. On the other hand, the compound of this invention possess little, if any, analgesic activity.

SUMMARY OF THE INVENTION

Accordingly, it is an object of this invention to provide novel 2-(4-aminobutoxy)stilbenes having superior anticonvulsant activity.

This and other objects of this invention as will hereinafter become clear have been attained by providing compounds of the formula (I):

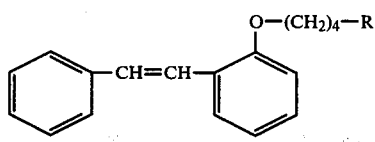

wherein R is

wherein $R_1$ and $R_2$ which are alike or different are selected from the group consisting of hydrogen and $C_1$-$C_5$ alkyl or

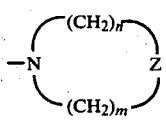

wherein Z is selected from the group consisting of

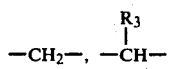

wherein $R_3$ is $C_1$-$C_5$ alkyl,

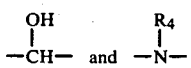

wherein $R_4$ is hydrogen, $C_1$-$C_5$ alkyl or $C_1$-$C_5$ hydroxyalkyl; m and n are each integers of 0 to 7; and m+n is an integer of 1 to 7, and the acid addition salts thereof.

This invention also relates to a method of treating convulsions and seizures or relieving skeletal muscle spasm in warm-blooded animals which comprises administering to said animals an effective amount for treatment of convulsions and seizures or relief of skeletal muscle spasm of a compound of the formula (I) or the acid addition salt thereof.

DESCRIPTION OF THE PREFERRED EMBODIMENTS

As summarized above, this invention relates to a group of compounds useful as pharmaceutical agents, which compounds are represented by the formula (I):

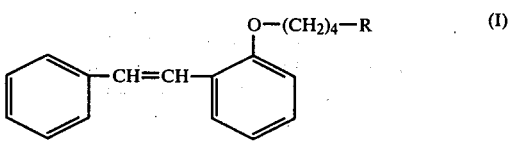

wherein R is

wherein $R_1$ and $R_2$ which are alike or different are selected from the group consisting of hydrogen and alkyl of 1–5 (preferably 1–3) carbon atoms such as methyl, ethyl, propyl, butyl or pentyl, or

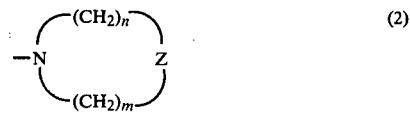

wherein Z is selected from the group consisting of

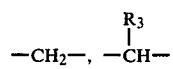

wherein $R_3$ is alkyl of 1–5 (preferably 1–3) carbon atoms such as methyl, ethyl, propyl or the like,

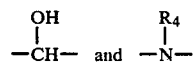

wherein $R_4$ is hydrogen, alkyl of 1–5 (preferably 1–3) carbon atoms such as methyl, ethyl, propyl or the like, and hydroxyalkyl of 1–5 (preferably 1–3) carbon atoms such as hydroxymethyl, 1-hydroxyethyl, 2-hydroxyethyl, 3-hydroxypropyl or the like; m and n are each integers of 0 to 7, preferably 0 to 5; and m+n is an integer of 1 to 7, preferably 2 to 5.

Suitable examples of R in the formula (I) include amino, methylamino, dimethylamino, propylamino, dipropylamino, aziridinyl, 1-azetidinyl, 1-pyrrolidinyl, piperidino, 4-methylpiperidino, 4-hydroxypiperidino, 3-hydroxypiperidino, hexahydro-1-azepinyl, 4-methyl-1-piperazinyl, 4-propyl-1-piperazinyl, 4-(2-hydroxyethyl)-1-piperazinyl, 1-imidazolidinyl, 1-pyrazolidinyl, 3-methyl-1-imidazolidinyl, 4-methylhexahydro-1,4-diazepin-1-yl, 4-(2-hydroxyethyl) hexahydro-1,4-diazepin-1-yl and the like.

Illustrative of the compounds of this invention are the following:
2-(4-aminobutoxy)stilbene
2-(4-methylaminobutoxy)stilbene
2-(4-dimethylaminobutoxy)stilbene
2-(4-ethylaminobutoxy)stilbene
2-(4-diethylaminobutoxy)stilbene
2-(4-propylaminobutoxy)stilbene
2-(4-dipropylaminobutoxy)stilbene
2-[4-(1-pyrrolidinyl)butoxy]stilbene
2-[4-(4-hydroxypiperidino)butoxy]stilbene
2-(4-piperidinobutoxy)stilbene
2-[4-(4-methylpiperidino)butoxy]stilbene
2-[4-(4-ethylpiperidino)butoxy]stilbene
2-[4-(hexahydro-1-azepinyl)butoxy]stilbene
2-[4-(4-hydroxypiperidino)butoxy]stilbene
2-[4-(3-hydroxypiperidino)butoxy]stilbene
2-[4-(4-propylpiperidino)butoxy]stilbene
2-[4-(4-methyl-1-piperazinyl)butoxy]stilbene
2-[4-(4-ethyl-1-piperazinyl)butoxy]stilbene
2-[4-(4-propyl-1-piperazinyl)butoxy]stilbene
2-[4-{4-(2-hydroxyethyl)-1-piperazinyl}butoxy]stilbene
2-[4-{4-(3-hydroxypropyl)-1-piperazinyl}butoxy]stilbene
2-[4-(2-methyl-1-pyrazolidinyl)butoxy]stilbene
2-[4-(4-methylhexahydro-1,4-diazepin-1-yl)butoxy]stilbene
2-[4-{4-(2-hydroxyethyl)hexahydro-1,4-diazepin-1-yl}butoxy]stilbene The pharmaceutically acceptable acid addition salts of the above compounds are, of course, also included within the scope of this invention.

It will be understood that the term "pharmaceutically acceptable acid addition salts" as used herein is intended to include non-toxic salts of the compounds of this invention with an anion. Representative of such salts are hydrochlorides, hydrobromides, sulfates, phosphates, nitrates, acetates, oxalates, succinates, adipates, propionates, tartrates, maleates, citrates, benzoates, toluenesulfonates, and methanesulfonates.

The compounds of this invention which are preferred due to their high level of anticonvulsant and muscle relaxant activity are those wherein R in the above formula (I) is

wherein $R_1$ and $R_2$ are each hydrogen or $C_1$-$C_3$ alkyl or

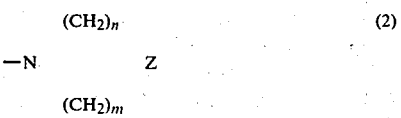

wherein Z is selected from the group consisting of

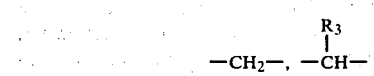

wherein $R_3$ is $C_1$-$C_3$ alkyl,

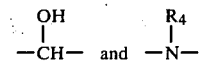

wherein $R_4$ is $C_1$-$C_3$ alkyl or $C_1$-$C_3$ hydroxyalkyl; m and n are each integers of 0 to 4; and m+n is an integer of 3 or 4.

Specific examples of the preferred compounds are those wherein R is a $C_1$-$C_3$ alkylamino or $C_2$-$C_6$ dialkylamino group, or a piperazinyl, piperidino or pyrrolidinyl group any of which is unsubstituted or substituted with a $C_1$-$C_4$ alkyl, hydroxy or $C_1$-$C_3$ hydroxyalkyl group.

Of the compounds of this invention, it will be understood that the following compounds are most preferred.
2-(4-dimethylaminobutoxy)stilbene
2-(4-methylaminobutoxy)stilbene
2-[4-(4-methyl-1-piperazinyl)butoxy]stilbene
2-[4-{4-(2-hydroxyethyl)-1-piperazinyl}butoxy]stilbene
2-(4-piperidinobutoxy)stilbene
2-[4-(3-hydroxypiperidino)butoxy]stilbene
2-[4-(1-pyrrolidinyl)butoxy]stilbene
2-[4-(4-propyl-1-piperazinyl)butoxy]stilbene The compounds of this invention are prepared by reacting a 2-(4-halogenobutoxy)stilbene of the formula (II):

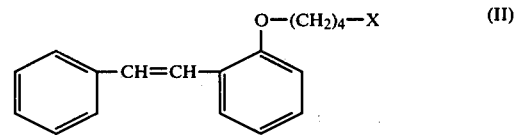

wherein X is halogen, with an amine having the formula (III):

wherein R is as defined in the formula (I).

The 2-(4-halogenobutoxy)stilbene starting material can be prepared by reacting a 2-hydroxystilbene with a 1,4-dihalogenobutane in the presence of a base.

The amine reacts with the equimolecular amount of the 2-(4-halogenobutoxy)stilbene.

However, the use of the excess amine accelerates the reaction. Normally, the amount of the amine to be employed is in the range of 1 to 100 moles, preferably 2 to 40 moles per mole of the 2-(4-halogenobutoxy)stilbene. A large amount of the amine serves also as a solvent.

The reaction can be carried out without an added solvent. However, the use of a reaction-inert solvent makes a homogeneous reaction possible.

Examples of such solvents are water, dioxane, tetrahydrofuran, dimethyl sulfoxide, lower aliphatic alcohols and the mixture thereof.

The reaction temperature is not critical, but normally ranges from room temperature to 150° C., preferably from room temperature to 100° C.

The reaction time varies widely with the reaction temperature and the reactivity of the starting materials, but normally is within 40 hours.

The presence of bases which neutralize a hydrogen halide formed in the course of the reaction accelerates the reaction. Examples of such bases are inorganic bases such as potassium hydroxide, sodium hydroxide, potassium carbonate, sodium carbonate and the like; and tertiary amines such as pyridine, triethylamine and the like.

The amount of the base to be employed is normally in the range of 1 to 5 moles per mole of the 2-(4-halogenobutoxy)stilbene.

When the base is absent, the 2-(4-aminobutoxy)stilbene reacts with a hydrogen halide formed during the reaction and are converted to the acid addition salt thereof. In order to obtain a suitable acid addition salt, the excess amine and the solvent are distilled off, an aqueous solution of a strong base such as sodium hydroxide and potassium hydroxide added to convert the acid addition salt of the 2-(4-aminobutoxy)stilbene to its free form, which is extracted with a solvent such as ether, chloroform and benzene, and then a suitable acid is added to neutralize its free form.

The 2-(4-aminobutoxy)stilbenes and the acid addition salts thereof which are the products of the above reactions may be purified by recrystallization employing a suitable solvent such as alcohol-ether.

The compounds of this invention which are useful as muscle relaxant and anticonvulsant agents can be administered by any means.

For example, administration can be parenterally, subcutaneously, intravenously, intramuscularly, or intraperitoneally. Alternatively or concurrently, administration can be by the oral route. The dosage administered will be dependent upon the age, health and weight of the recipient, the extent of convulsions, seizures or skeletal muscle spasm, kind of concurrent treatment if any, frequency of treatment, and the nature of the effect desired. Generally, a daily dosage of the active ingredient compound will be from about 0.5 to 50 mg per kg of body weight. Normally, from 1 to 30 mg per kg per day, in one or more applications per day is effective to obtain the desired result.

The compound of Formula I can be employed in dosage forms such as tablets, capsules, powder packets, or liquid solutions, suspensions, or elixirs, for oral administration, or sterile liquid formulations such as solutions or suspensions for parenteral use.

Besides the active ingredient of this invention, the composition will contain a solid or liquid non-toxic pharmaceutical carrier for the active ingredient. In one embodiment of a composition, the solid carrier can be a capsule of the ordinary gelatin type. In another embodiment, the active ingredient can be tableted with or without adjuvants, or put into powder packets. These capsules, tablets and powders will generally constitute from about 5% to about 95% and preferably from 25% to 90% by weight of the active ingredient. These dosage forms preferably contain from about 5 to about 500 mg of active ingredients, with from about 25 to about 250 mg being most preferred.

The pharmaceutical carrier can be a sterile liquid such as water and oils, including those of petroleum, animal, vegetable or synthetic origin, such as peanut oil, soybean oil, mineral oil, sesame oil, and the like.

In general, water saline, aqueous dextrose and related sugar solutions, and glycols such as polyethylene glycol are preferred liquid carriers, particularly for injectible solutions such as saline will ordinarily contain from about 0.5% to 20% and preferably about 1 to 10% by weight of the active ingredient.

As mentioned above, oral administration can be in a suitable suspension or syrup, in which the active ingredient normally will constitute from about 0.5 to 10% by weight.

The pharmaceutical carrier in such composition can be a watery vehicle such as an aromatic water, a syrup or a pharmaceutical mucilage.

The procedures employed for demonstrating anticonvulsant efficacy of the compounds as set forth in the following examples are as follows:

Animals used were ddy strain male mice (20–22 g) and Wistar strain male rats (150–170 g).

Anticonvulsant actions were determined by the ability of the compounds to prevent pentylenetetrazol (PTZ) convulsion and maximal electroshock seizure (MES), using 8 mice per group. Anti-PTZ action was judged by the protection against tonic extensor (TE) induced by intraperitoneal injection of PTZ (100 mg/kg i.p.) (K. Nakamura et al., Arch. int. Pharmacodyn., 156 261 (1965)).

Anti-MES action was also judged by the protection against TE induced by electroshock via a pair of ear electrodes (J. J. Piala et al., J. Pharmacol. exp. Therap., 127 55 (1959)).

The results were expressed as 50% effective dose ($ED_{50}$, mg/kg po) or an inhibition percentage at certain doses used.

$LD_{50}$ was calculated by the method of Litchfield-Wilcoxon (J. T. Litchfield and F. Wilcoxon, J. Pharmacol. exp. Therap., 96 99 (1949)).

Using the above procedures the compounds of this invention were compared to well known antiepileptic agents, methotoin which is effective against grand-mal seizure and trimethadione which is effective against peti-mal seizure.

The results are shown in Table 2.

The following examples are presented to further illustrate the preparation of the compounds of this invention.

EXAMPLE 1

A solution of 5.0 g of 2-(4-bromobutoxy)stilbene, 50 ml of 50% dimethylamine aqueous solution and 50 ml of tetrahydrofuran is stirred at room temperature for 20 hours. At the end of this period, tetrahydrofuran and excess dimethylamine are distilled in vacuo, 2 N-NaOH aqueous solution is added, and the reaction product is extracted with ether. The ether solution is washed with saturated sodium chloride solution and dried over anhydrous sodium sulfate. The addition of 20% HCl/ethanol gives a precipitate which is filtered and then crystallized to yield 4.6 g (92%) of 2-(4-dimethylaminobutoxy)stilbene hydrochloride, m.p. 60°–68° C.

Analysis—Calcd. for $C_{20}H_{25}NO \cdot HCl$ (percent): C, 72.38; H, 7.90; N, 4.38 Found (percent): C, 72.20; H, 8.23; N, 4.30.

Various 2-(4-aminobutoxy)stilbenes were prepared according to the procedure described in Example 1 using the appropriate starting materials. The results are summarized in Table 1.

TABLE 1

Structure: Ph—CH=CH—C₆H₄(o-O(CH₂)₄—R)

| No. | —R | Addition moiety | m.p. (°C.) | C (Calcd/Found) | H (Calcd/Found) | N (Calcd/Found) |
|---|---|---|---|---|---|---|
| 1 | —N(CH₃)₂ | HCl | 60 | 72.38 / 72.20 | 7.90 / 8.23 | 4.38 / 4.30 |
| 2 | —N(C₂H₅)₂ | HCl | 139–140 | 73.41 / 73.72 | 8.40 / 8.44 | 3.89 / 3.73 |
| 3 | —N(H)(CH₃) | HCl | 170–171 | 71.80 / 72.06 | 7.61 / 7.72 | 4.41 / 4.44 |
| 4 | —N(piperazinyl)—CH₂CH₂OH | 2HCl | 187–191 | 63.57 / 63.65 | 7.56 / 7.32 | 6.18 / 6.35 |
| 5 | —N(piperidinyl) | HCl | 130–132 | 74.27 / 74.31 | 8.13 / 8.08 | 3.77 / 3.90 |
| 6 | —N(piperazinyl)—NCH₃ | 2HCl | 215–217 | 65.24 / 65.38 | 7.62 / 7.58 | 6.62 / 6.73 |
| 7 | —N(pyrrolidinyl) | HCl | 135–136 | 72.82 / 73.71 | 7.22 / 7.92 | 3.94 / 3.79 |
| 8 | —N(3-hydroxypiperidinyl) | HCl | 146–147 | 71.21 / 71.35 | 7.79 / 7.95 | 3.61 / 3.53 |
| 9 | —N(4-hydroxypiperidinyl) | HCl | 152–155 | 71.21 / 71.22 | 7.79 / 7.86 | 3.61 / 3.87 |
| 10 | —N(piperazinyl)—NCH₂CH₂CH₃ | 2HCl | 213–214 | 66.96 / 66.83 | 7.42 / 7.36 | 6.25 / 6.21 |
| 11 | —N(4-methylpiperidinyl)—CH₃ | HCl | 141–143 | 74.68 / 74.73 | 8.36 / 8.51 | 3.63 / 3.92 |

TABLE 2

Structure: Ph—CH=CH—C₆H₄(o-O(CH₂)₄—R)

| No. | —R | Anti-MES $ED_{50}$ (mg/kg PO) | Anti-PTZ $ED_{50}$ (mg/kg PO) | $LD_{50}$ Mice (mg/kg PO) | $LD_{50}$ Rat (mg/kg PO) |
|---|---|---|---|---|---|
| 1 | —N(CH₃)₂ | 38.0 | 17.8 | 1,300 | 2,000 |
| 2 | —NHCH₃ | 60.0 | 22.5 | 839 | — |
| 3 | —N(piperazinyl)—NCH₃ | 35.5 | 21.1 | 1,050 | 2,300 |
| 4 | —N(piperazinyl)—NCH₂CH₂OH | 76.1 | 16.3 | 1,050 | — |

TABLE 2-continued

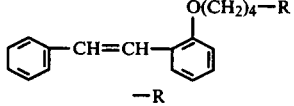

| No. | —R | Anti-MES ED$_{50}$ (mg/kg PO) | Anti-PTZ ED$_{50}$ (mg/kg PO) | LD$_{50}$ (mg/kg PO) Mice | Rat |
|---|---|---|---|---|---|
| 5 | 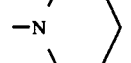 | 60.0 | <50* (100%) | 621 | — |
| 6 | 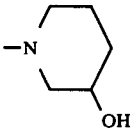 | 20.0 | 14.0 | 415 | — |
| 7 | 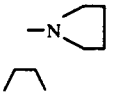 | 65.0 | <50* (87.5%) | 600 | — |
| 8 |  | 50* (40%) | <50* (85%) | — | |
| 9 | Methotoin | 91.3 | 51.9 | 475 | 2,500[a] |
| 10 | Trimethadione | 1,180 | 230 | 2,200 | — |

*Inhibition %
[a]described in a book named "Iyakuhin Kenkyuho" (page 258) published by "Asakura Shoten" (1968)

As is apparent from Table 2, the antiepileptic efficacy of the compounds Nos. 1, 3 and 6 in Table 2 is much greater than that of trimethadione and methotoin. It is to be noted that the compounds Nos. 1 and 3 are preferred due to their low level of toxicity.

Having now fully described the invention, it will be apparent to one of ordinary skill in the art that many changes and modifications can be made thereto without departing from the spirit of the invention as set forth herein.

What is claimed as new and intended to be covered by Letters Patent is:

1. A compound having the formula:

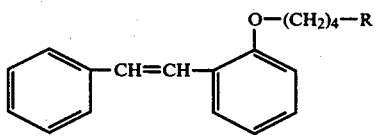

wherein R is

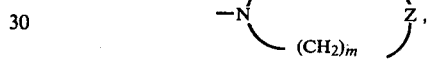

wherein Z is selected from the group consisting of —CH$_2$—, —CR$_3$H—, said R$_3$ being C$_1$–C$_5$ alkyl, and —CHOH—; and wherein m and n are each integers of 0 to 4 with m+n being equal to 4, or the acid addition salts thereof.

2. The compound of claim 1, wherein R is piperidino or piperidino substituted with a C$_1$–C$_4$ alkyl or hydroxy.

3. The compound of claim 2, wherein said R is piperidino.

4. The compound of claim 2, wherein said R is 4-hydroxypiperidino or 3-hydroxypiperidino.

5. The compound of claim 2, wherein said R is 4-methylpiperidino.

6. A pharmaceutical composition for use as a skeletal muscle relaxant or anticonvulsant agent, comprising a pharmaceutically effective amount of the compound of claim 1 and a pharmaceutically acceptable carrier.

7. A method of treating convulsions and seizures or relieving skeletal muscle spasm in warm-blooded animals which comprises administering to said animals an effective amount for treatment of convulsions and seizures or relief of skeletal muscle spasm of a compound of claim 1 or the acid addition salt thereof.

* * * * *

UNITED STATES PATENT AND TRADEMARK OFFICE
CERTIFICATE OF CORRECTION

PATENT NO. : 4,284,637

DATED : Aug. 18, 1981

INVENTOR(S) : RYOJI KIKUMOTO ET AL

It is certified that error appears in the above-identified patent and that said Letters Patent are hereby corrected as shown below:

Please insert the Priority Data to read as follows:

[30]--Foreign Application Priority Data

March 9, 1978 [JP] Japan... 53-26906

Signed and Sealed this

First Day of December 1981

[SEAL]

Attest:

GERALD J. MOSSINGHOFF

Attesting Officer    Commissioner of Patents and Trademarks